United States Patent
Hickey et al.

(10) Patent No.: US 10,350,375 B2
(45) Date of Patent: Jul. 16, 2019

(54) DEVICES, SYSTEMS AND METHODS FOR FACILITATING FACEMASK COMPLIANCE

(71) Applicants: Anthony James Hickey, Chapel Hill, NC (US); Timothy M. Crowder, Durham, NC (US)

(72) Inventors: Anthony James Hickey, Chapel Hill, NC (US); Timothy M. Crowder, Durham, NC (US)

(73) Assignee: Astartein, LLC, Chapel Hill, NC (US)

( * ) Notice: Subject to any disclaimer, the term of this patent is extended or adjusted under 35 U.S.C. 154(b) by 869 days.

(21) Appl. No.: 14/985,832

(22) Filed: Dec. 31, 2015

(65) Prior Publication Data

US 2016/0106941 A1    Apr. 21, 2016

Related U.S. Application Data (63) Continuation-in-part of application No. PCT/US2013/049268, filed on Jul. 3, 2013.

(51) Int. Cl.
*A61M 16/06* (2006.01)
*A61M 16/00* (2006.01)
(Continued)

(52) U.S. Cl.
CPC ........ *A61M 16/06* (2013.01); *A61M 15/0086* (2013.01); *A61M 16/0051* (2013.01);
(Continued)

(58) Field of Classification Search
CPC combination set(s) only.
See application file for complete search history.

(56) References Cited

U.S. PATENT DOCUMENTS 6,240,921 B1 * 6/2001 Brydon ............. A61M 16/0051
128/204.18
6,349,724 B1 * 2/2002 Burton ............. A61M 16/0057
16/57

(Continued)

FOREIGN PATENT DOCUMENTS

EP          0 661 071        7/1995
WO      WO 99-30760 A1      6/1999
(Continued)

OTHER PUBLICATIONS

Notice of Decision to Grant for corresponding EP application No. 13888727.8 dated May 25, 2018, 2 pages.
(Continued)

*Primary Examiner* — Gregory A Anderson
*Assistant Examiner* — Margaret M Luarca
(74) *Attorney, Agent, or Firm* — Myers Bigel, P.A.

(57) ABSTRACT

A facemask includes a facemask body, a plurality of electrical contacts and a control circuit. The facemask body has an end including an opening and a skin contact perimeter extending along a periphery of the opening, with the skin contact perimeter configured to sealingly engage with a user's face. Each electrical contact is disposed at a respective region of the skin contact perimeter, and each electrical contact is configured to sense when the respective region of the skin contact perimeter is sealingly engaged with a user's face. The control circuit is disposed on the facemask body, and the control circuit is configured to receive a signal from each electrical contact when the respective region of the skin contact perimeter is sealingly engaged with a user's face and to initiate output of an audible stimulus and/or a visual stimulus in response to receiving a concurrent signal from all of the plurality of electrical contacts.

14 Claims, 9 Drawing Sheets

(51) Int. Cl.
  *A61M 15/00* (2006.01)
  *A61M 21/00* (2006.01)
  *A61M 11/02* (2006.01)
  *A61M 21/02* (2006.01)
(52) U.S. Cl.
  CPC .......... *A61M 16/021* (2017.08); *A61M 21/00* (2013.01); *A61M 11/02* (2013.01); *A61M 15/009* (2013.01); *A61M 16/0063* (2014.02); *A61M 21/02* (2013.01); *A61M 2021/005* (2013.01); *A61M 2021/0027* (2013.01); *A61M 2021/0044* (2013.01); *A61M 2205/13* (2013.01); *A61M 2205/18* (2013.01); *A61M 2205/3561* (2013.01); *A61M 2205/3584* (2013.01); *A61M 2205/3592* (2013.01); *A61M 2205/43* (2013.01); *A61M 2205/502* (2013.01); *A61M 2205/52* (2013.01); *A61M 2205/581* (2013.01); *A61M 2205/583* (2013.01); *A61M 2205/587* (2013.01); *A61M 2205/59* (2013.01); *A61M 2205/8206* (2013.01)

(56) References Cited

U.S. PATENT DOCUMENTS

| | | | | |
|---|---|---|---|---|
| 7,625,345 | B2 * | 12/2009 | Quinn | .................... A61B 5/091 482/13 |
| 2003/0192547 | A1 | 10/2003 | Lurie et al. | |
| 2005/0263150 | A1 | 12/2005 | Chathampally et al. | |
| 2013/0032148 | A1 * | 2/2013 | Neely | .................... A61M 16/06 128/204.18 |
| 2013/0032153 | A1 * | 2/2013 | Neely | .................... A61M 16/06 128/205.25 |
| 2015/0059739 | A1 * | 3/2015 | Aslam | ................. A61M 15/009 128/202.22 |

FOREIGN PATENT DOCUMENTS

| WO | WO 01-43804 A1 | 6/2001 |
|---|---|---|
| WO | WO 2010-045408 A2 | 4/2010 |

OTHER PUBLICATIONS

Notice of Acceptance for Patent Application for corresponding AU application No. 2013393313 dated Apr. 6, 2018, 3 pages.
International Preliminary Report on Patentability for corresponding PCT Application No. PCT/US2013/049268, dated Jan. 14, 2016 (11 pages).
Extended European Search Report for corresponding EP application No. 13888727.8 dated Jan. 26, 2017, 9 pages.
Notification of Transmittal of the International Search Report and the Written Opinion of the International Searching Authority, or the Declaration, in corresponding PCT Application No. PCT/US2013/049268, dated Apr. 3, 2014 (15 pages).

* cited by examiner

DEVICES, SYSTEMS AND METHODS FOR FACILITATING FACEMASK COMPLIANCE

RELATED APPLICATIONS

This is a continuation-in-part of International Patent Application No. PCT/US2013/049268, filed Jul. 3, 2013, the disclosure of which is hereby incorporated by reference in its entirety.

BACKGROUND

Treatment of disease with inhaled aerosols in young children can be difficult. The time required for nebulized aerosols to deliver an effective dose, the "mist" generated and/or the noise of the nebulizer pump can distract and/or frighten a child and result in the child removing the facemask. Boredom and discomfort are additional reasons that a child may remove the facemask. For air jet nebulizers, this often results in wasted drug, which is vented to atmosphere. In addition to waste, efficacy and delivery efficiency are negatively affected. Further, there may be negative facial and/or ocular effects due to the drug being deposited outside the facemask.

In addition, the transition from nebulized drugs to those delivered by a metered dose inhaler (MDI) with a spacer and facemask can be difficult due to the newness of the experience and the difference in sensation of inhaling propellant-based aerosols. As a result, children may remove the facemask leading to the same drawbacks described above.

SUMMARY

Some embodiments of the present invention are directed to a facemask. The facemask includes a facemask body having a first end including an opening configured to receive at least a portion of a user's face and a skin contact perimeter extending along a periphery of the opening. The skin contact perimeter is configured to sealingly engage with a user's face. The facemask includes a plurality of electrical contacts, with each electrical contact disposed at a respective region of the skin contact perimeter. Each electrical contact is configured to sense when the respective region of the skin contact perimeter is sealingly engaged with a user's face. A control circuit is disposed on the facemask body. The control circuit is configured to receive a signal from each electrical contact when the respective region of the skin contact perimeter is sealingly engaged with a user's face. The control circuit is configured to initiate output of an audible stimulus and/or a visual stimulus in response to receiving a concurrent signal from all of the plurality of electrical contacts.

The facemask body may include a port configured to receive medicament from a medicament delivery device, wherein the opening and the port are in fluid communication such that medicament received in the port can be delivered to the opening. The port may be configured to operatively connect with at least one of a nebulizer and a metered dose inhaler (MDI) spacer. The facemask body may define a cavity, with at least a portion of the cavity extending between the opening and the port.

In some embodiments, the facemask includes a speaker disposed on the facemask body, and the control circuit is configured to control the speaker to output an audible stimulus. The control circuit may be configured to control the speaker to output a children's melody and/or song as the audible stimulus.

In some embodiments, the facemask includes at least one light emitting diode (LED) disposed on the facemask body, with the control circuit configured to illuminate the at least one LED as a visual stimulus. The facemask may include a plurality of LEDs, with the control circuit configured to illuminate the LEDs in a sequence as the visual stimulus. In some embodiments, the facemask includes a speaker disposed on the facemask body and a plurality of LEDs disposed on the facemask body, and the control circuit is configured to control the speaker to output an audible stimulus and illuminate the LEDs as a visual stimulus.

The control circuit may be configured to stop the audible stimulus and/or visual stimulus when one of the electrical contacts does not sense that the respective portion of the skin contact perimeter is sealingly engaged with a user's face.

The facemask may include a power source disposed on the facemask body. Each electrical contact may be a switch configured to be actuated when the respective region of the skin contact perimeter is sealingly engaged with a user's face, and the switches may be configured to electrically connect the power source and the control circuit such that, when all the switches are concurrently actuated, the power source is electrically connected with the control circuit to initiate output of the audible stimulus and/or the visual stimulus. In some embodiments, at least three switches are spaced-apart along the skin contact perimeter. The switches may be positioned such that, when the facemask is sealingly engaged with a user's face, one of the switches is actuated by the bridge of the user's nose and two of the switches actuated by the user's face on opposite sides of the user's mouth. In some other embodiments, each electrical contact is a capacitive sensor configured to detect contact with skin.

The facemask may include a timer configured to measure an amount of time that a concurrent signal is received from all the plurality of electrical contacts. The timer may be configured to initiate output of an alarm signal when the measured amount of time reaches a threshold value and/or does not reach a threshold value. The facemask may include a memory configured to store data received from the timer.

In some embodiments, the facemask includes a transmitter disposed on the facemask body, with the transmitter being configured to transmit a wireless signal to an outside device that is configured to output the audible stimulus and/or the visual stimulus. In some embodiments, the facemask includes a transmitter disposed on the facemask body, with the transmitter configured to transmit a wireless signal to an outside device when a concurrent signal is received from all the plurality of electrical contacts such that the outside device can display and/or record data based on the wireless signal. In some embodiments, the facemask is configured to be wiredly connected to an outside device that is configured to output the audible stimulus and/or the visual stimulus.

The facemask may be used in combination with a nebulizer assembly including a chamber configured to hold liquid medicament and a pump in fluid communication with the chamber. The pump is configured to supply pressurized fluid to the chamber to form an aerosol, and the chamber is in fluid communication with the port of the facemask body.

The facemask may be used in combination with an MDI spacer having a body including first and second opposite end portions, with the first end portion of the spacer adapted to receive an MDI, and with the second end portion operatively connected to the port of the facemask body. A plurality of LEDs may be disposed on the spacer body, with the control circuit configured to illuminate the LEDs as the visual stimulus. At least one light string may be disposed around a circumference of the spacer body and/or along a length of the spacer body, with the control circuit configured to illuminate the at least one light string as the visual stimulus.

Some embodiments of the present invention are directed to methods for improving juvenile compliance with inhaled medication administration. The method includes providing a facemask. The facemask includes a body having an opening at an end thereof with a skin contact perimeter arranged around the opening and at least three switches in a spaced-apart relationship at the skin contact perimeter. The facemask also includes at least one output device in electrical communication with the switches and configured to output an audible stimulus and/or a visual stimulus. The method includes receiving at least a portion of a child's face in the opening. The method includes outputting an audible stimulus and/or a visual stimulus from the at least one output device in response to concurrent actuation of all switches indicating that the skin contact perimeter is sealingly engaged with the child's face. The method includes halting the audible stimulus and/or the visual stimulus from the at least one output device when at least one of the switches is not actuated indicating that at least a portion of the skin contact perimeter is not sealingly engaged with the child's face.

Some embodiments of the present invention are directed to methods for improving juvenile compliance with inhaled medication administration. The method includes providing a facemask. The facemask includes a facemask body including an opening configured to receive at least a portion of a child's face and a skin contact perimeter extending along a periphery of the opening. The skin contact perimeter configured to sealingly engage with the child's face. The facemask includes at least three electrical contacts, with each electrical contact disposed at a respective region of the skin contact perimeter, and with each electrical contact configured to sense when the respective region of the skin contact perimeter is sealingly engaged with the child's face. The facemask includes a control circuit in or on the facemask body and configured to receive a signal from each electrical contact when the skin contact perimeter is sealingly engaged with a child's face. The facemask includes a transmitter in or on the facemask, with the transmitter configured to transmit a wireless signal to an outside device in response to receiving a concurrent signal from all of the electrical contacts. The facemask has a a themed appearance. The method further includes: receiving at least a portion of a child's face in the opening; transmitting a wireless signal from the transmitter to the outside device in response to concurrent actuation of all of the electrical contacts indicating that the skin contact perimeter is sealingly engaged with the child's face; and initiating a game on the outside device in response to the transmitter transmitting the wireless signal to the outside device, with the game having a theme that corresponds to the theme of the facemask.

The method may include halting or pausing the game on the outside device when at least one of the electrical contacts is not actuated indicating that at least a portion of the skin contact perimeter is not sealingly engaged with the child's face.

The method may include: measuring an amount of time that a concurrent signal is received from all the plurality of electrical contacts; and ending the game when the measured amount of time reaches a threshold value.

In some embodiments, the facemask includes at least one of a headset and a visor fixedly or releasably attached to the body to provide a pilot theme and the game is a flying or pilot game. In some embodiments, the facemask comprises an eye mask or goggles integrated with or releasably attached to the facemask body to provide a scuba theme and the game is a diving or scuba game.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EMBODIMENTS OF THE INVENTION

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the expression "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
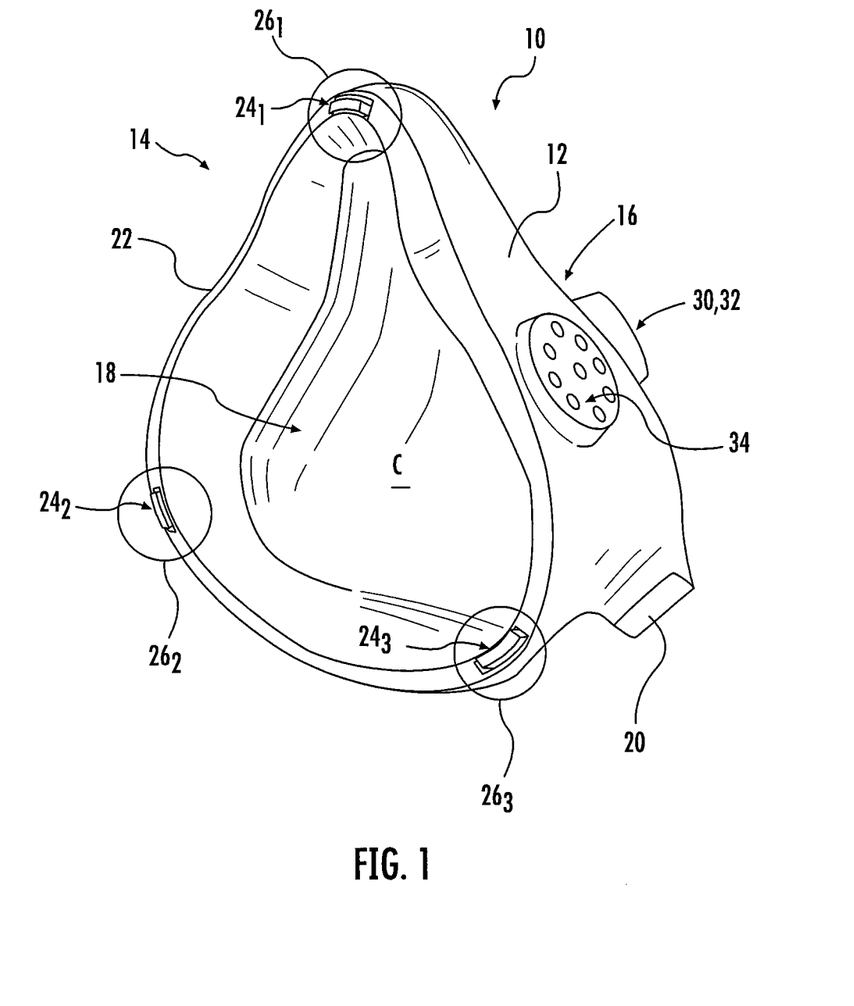
FIG. 1 is a perspective view of a facemask according to some embodiments of the invention.

Generally stated, embodiments of the invention provide facemasks that provide audio or visual outputs when the facemask is sealingly engaged with a patient's face. A facemask 10 according to some embodiments of the invention is shown in FIG. 1. The facemask 10 includes a body or shell 12 having a first or rear end 14 that contacts a face of a patient and an opposing second or forward end 16. The body 12 defines a cavity C. The body 12, and therefore the cavity C, tapers from the first end 14 to the second end 16. An opening 18 is defined at the first end 14 of the body 12. The opening 18 is configured to receive a portion of a patient's or user's face such that the nose is disposed in the cavity C.

Figure 4:
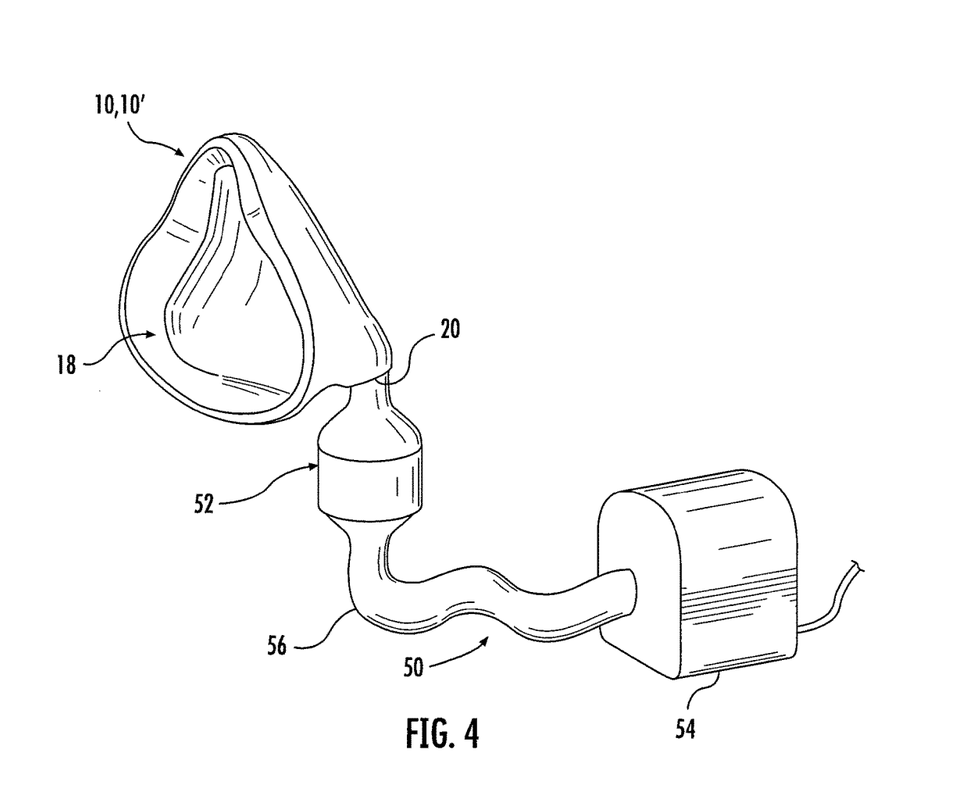
FIG. 4 is a perspective view of a facemask connected with a nebulizer according to some embodiments of the invention.

The body 12 includes a port 20 configured to receive medicament from a medicament delivery device. In position, medicament may be received at the port 20, flow through at least a portion of the cavity C, and be inhaled by a patient or user. The port 20 may face in a direction generally perpendicular to the opening 18 (for example, generally downwardly facing as shown in FIGS. 1 and 4), which may be a desired orientation for use with a nebulizer. Alternatively, the port 20 may be positioned at the second end 16 of the facemask body 12 (FIG. 5), which may be a desired orientation for use with a spacer or a valved holding chamber used in connection with a metered dose inhaler (MDI) or pressurized metered dose inhaler (pMDI). It is contemplated that the port 20 may be positioned on or extend from the facemask body 12 in any orientation and/or position, e.g., at the second end 16 of the body 12 or between the second end 16 of the body 12 and the first end 14 of the body 12.

Still referring to FIG. 1, the facemask 10 includes a skin contact perimeter 22 at the first end 14 of the body 12. The perimeter 22 is configured to sealingly engage with a patient's or user's face. That is, as the facemask 10 is brought toward the patient's face, a portion of the patient's face is received through the opening 18, and the skin contact perimeter 22 seals against the patient's face (e.g., seals against the nose, cheek and/or chin regions). The skin contact perimeter 22 extends along a periphery of the opening 18 and is typically curvilinear and may include a triangulated incline to accommodate a nose of a patient. Although not illustrated, the facemask 10 may include a strap which, as known to those of skill in the art, may be configured to loop around a back or rear of a patient's head to help keep the facemask in place during use.

The facemask body 12 may be formed as a single monolithic piece such that the first end 14 of the body 12 defines the skin contact perimeter 22. The body 12 may be formed of a flexible, resilient material so as to conform to the patient's face and provide a tight seal. In some other embodiments, the skin contact perimeter 22 may be separate contact component or member that is attached to the first end 14 of the body 12. In this regard, the skin contact perimeter 22 may be formed of a flexible, resilient material and the body 12 may be formed of a somewhat more rigid material. If the skin contact perimeter 22 is a separate contact component or member, it can be integrally or releasably attached.

A plurality of spaced-apart electrical contacts or inputs (e.g., sensors and/or switches) are disposed about the skin contact perimeter 22. The electrical contacts or inputs may be attached to an outer surface of the skin contact perimeter 22 or may be at least partially embedded in the perimeter 22 and/or the facemask body 12. Three spaced-apart electrical contacts or inputs $24_1$, $24_2$, $24_3$ are shown in the embodiment illustrated in FIG. 1. Each electrical contact or input $24_1$, $24_2$, $24_3$ is disposed at a corresponding edge region $26_1$, $26_2$, $26_3$ of the skin contact perimeter 22. Each electrical contact or input $24_1$, $24_2$, $24_3$ is configured to sense when its corresponding region $26_1$, $26_2$, $26_3$ of the skin contact perimeter 22 is in contact with the patient's face. When all three electrical contacts or inputs $24_1$, $24_2$, $24_3$ are in contact, the skin contact perimeter 22 can be identified as in proper sealed engagement.

Figure 2:
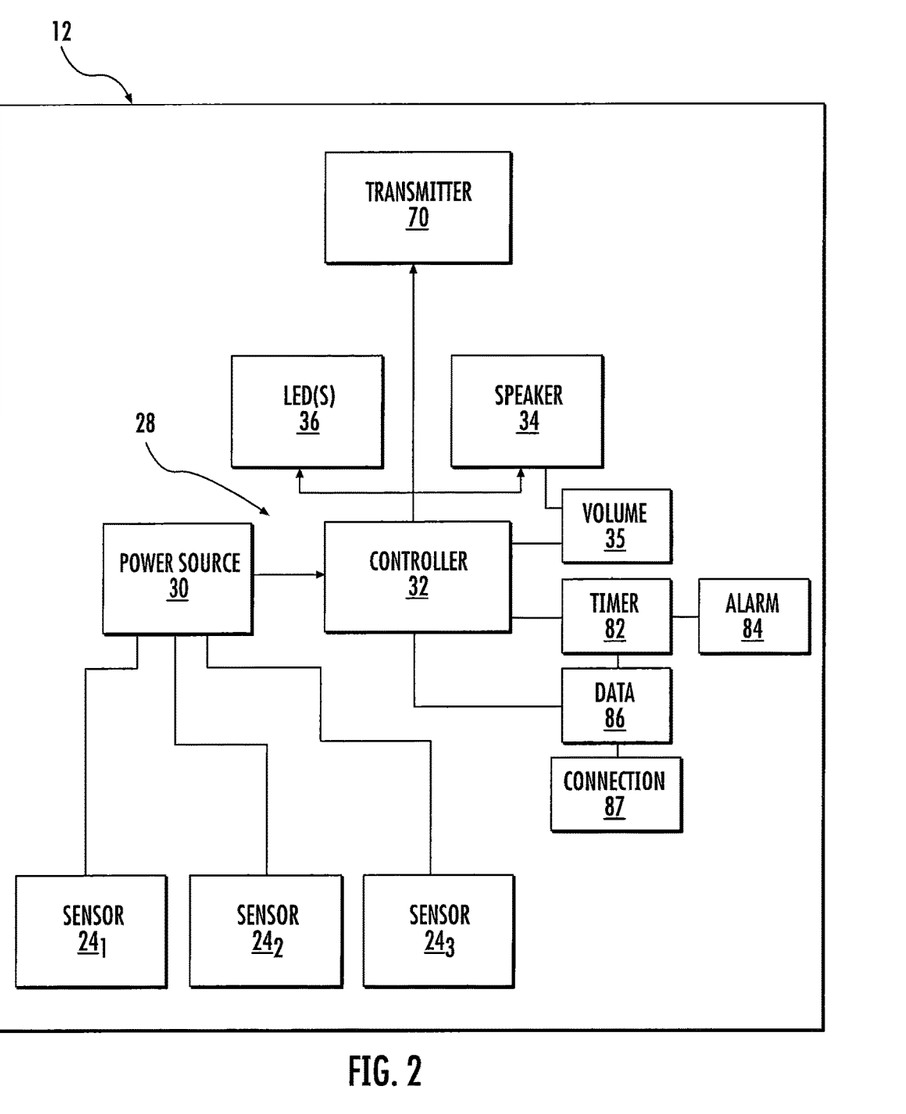
FIG. 2 is a block diagram illustrating components used in facemasks according to some embodiments of the invention.

Turning to FIG. 2, the facemask 10 may include or be in communication with a control circuit 28. The control circuit 28 may include a power source 30 (e.g., a battery) and/or a controller 32 (e.g., a microcontroller or a microprocessor). The power source 30 and/or the controller 32 may be disposed on the facemask body 12, as shown in FIG. 1. The power source 30 and/or the controller 32 may be attached to an outer surface of the body 12 or may be at least partially embedded in the body 12 or may be suspended or otherwise attached to the facemask 10 or a strap associated therewith. The control circuit 28 is configured to monitor and/or receive a signal from each of the electrical contacts or inputs $24_1$, $24_2$, $24_3$ that indicates that the corresponding region $26_1$, $26_2$, $26_3$ of the skin contact perimeter 22 is in contact with skin and thus sealingly engaged with the patient's face.

The control circuit 28 is configured to initiate output of an audible stimulus and/or a visual stimulus in response to receiving a concurrent signal from each of the plurality of electrical contacts or inputs $24_1$, $24_2$, $24_3$. For example, in the embodiment shown in FIG. 1, the control circuit 28 (or the controller 32) can be configured to send a signal to a speaker 34 such that the speaker outputs an audible stimulus. As illustrated, the speaker 34 may be disposed on the facemask body 12. The speaker 34 may be attached to an outer surface of the body 12 or may be at least partially embedded in the body 12 or may be suspended or otherwise attached to the facemask 10 or a strap associated therewith (e.g., the speaker 34 may be attached as an earpiece). Any suitable speaker may be employed; an exemplary suitable speaker is a piezo speaker.

The audible stimulus may be a melody or song that is particularly pleasing, soothing and/or stimulating to a child, and therefore may encourage the child to retain the facemask in a sealing relationship with his or her face. The melody or song may be stored on the controller 32. In some embodiments, the controller 32 stores a plurality melodies and/or songs. The controller 32 may control the speaker 34 to output different melodies in a predetermined or a random sequence. In some embodiments, the controller 32 and/or the speaker 34 is or includes a melody integrated circuit. In some embodiments, the melodies/songs may be customized and user selectable via a display or other input. For example, the melodies/songs may be downloaded and/or selected using a computer, electronic notepad, smartphone, etc.

The volume of the audible stimulus may be adjustable or controllable, for example using a volume control 35 (FIG. 2). The volume control 35 may be or include button(s), a dial or the like. The volume control 35 may be disposed on the facemask body 12 or elsewhere as described above in connection with the speaker 34. The controller 32 may adjust the signal sent to the speaker 34 and/or the output of the speaker 34 in response to adjustment of the volume control 35. The volume control 35 may be adjusted by the patient, a caregiver and/or supervising staff. For example, it may be desirable for a supervising staff member to adjust the volume to accommodate the wishes of a child patient. Generally speaking, the volume control 35 may be included to allow for adjustment of the volume of the audible stimulus to an appropriate level for the hearing of the patient (e.g., a child patient).

Figure 3:
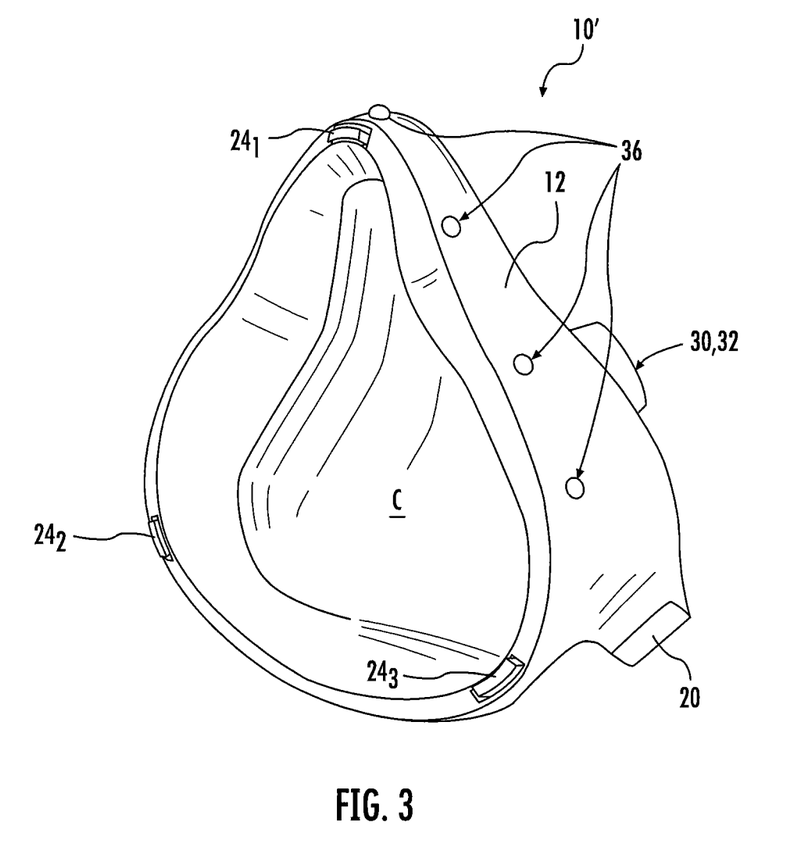
FIG. 3 is a perspective view of a facemask according to some other embodiments of the invention.

A facemask 10' according to some embodiments is illustrated in FIG. 3. The facemask 10' includes all the same features of the facemask 10 of FIG. 1 with the speaker 34 being optional. The facemask 10' includes a plurality of visual indicators 36, such as light emitting diodes (LEDs), disposed on the facemask body 12. The LEDs 36 may be attached to an outer surface of the body 12 or may be at least partially embedded in the body 12. The LEDs 36 may be disposed in a spaced-apart relationship along at least a portion of a periphery of the body 12, along at least a major portion of the periphery of the body, and along the entire or substantially the entire periphery of the body in various embodiments.

In response to receiving a concurrent signal from each of the plurality of electrical contacts or inputs $24_1$, $24_2$, $24_3$, the control circuit 28 (or the controller 32) is configured to illuminate the LEDs 36 to output a visual stimulus. The controller 32 may be configured to illuminate the LEDs 36 in a particular or predetermined sequence; for example, adjacent LEDs 36 may illuminate sequentially in one direction, giving the effect that the emitted light is "circling" the facemask body 12. Other predetermined sequences are contemplated; it is also contemplated that the controller 32 may illuminate the LEDs 36 in a random duration and/or order. Additionally or alternatively, the LEDs 36 may be of varying color. The visual stimulus created by the LEDs 36 may be particularly pleasing, soothing and/or stimulating to a child, and therefore may encourage the child to retain the facemask in a sealing relationship with his or her face.

The various features of the facemask 10 (FIG. 1) and the facemask 10' (FIG. 3) may be combined. In particular, the facemask 10 may include the speaker 34 and the LEDs 36 to therefore provide both audible and visual stimuli in response to receiving a concurrent signal from each of the plurality of electrical contacts or inputs $24_1$, $24_2$, $24_3$. The audible and visual stimuli may be provided consecutively. For example, the controller 32 may be configured to control the output of the speaker 34 to play a melody and at the same time configured to control the LEDs 36 such that one or more of the LEDs 36 illuminates for each tone of the melody (e.g., a different LED or set of LEDs and/or colors of LEDs for each tone). Although only one controller 32 is illustrated, it is contemplated that more than one controller may be employed (e.g., one to control output of the speaker 34 and one to illuminate the LEDs 36).

In some embodiments, the electrical contacts or inputs $24_1$, $24_2$, $24_3$ are switches. Each switch $24_1$, $24_2$, $24_3$ is configured to be actuated in response to sealing engagement of the corresponding region $26_1$, $26_2$, $26_3$ (FIG. 1) of the skin contact perimeter 22 and the patient's face. When all switches $24_1$, $24_2$, $24_3$ are concurrently actuated, the power supply 30 is electrically connected to and supplies power to the controller 32, which in turn causes the controller to control the output of the speaker 34 and/or the LEDs 36. In some other embodiments, the electrical contacts or inputs $24_1$, $24_2$, $24_3$ are contact sensors configured to sense contact with skin (i.e., the patient's face); for example, the sensors $24_1$, $24_2$, $24_3$ may be capacitive sensors.

The facemasks 10, 10' may be suitable for use with a nebulizer. Turning to FIG. 4, the facemasks 10, 10' are shown in use with a nebulizer assembly 50. The nebulizer assembly 50 can include a nebulizer or a nebulizer chamber 52 in which medicine is held. The medicine can be in liquid formulation or other suitable formulation. A compressor or pump 54 is connected to the nebulizer 52 by tubing 56. The pump 54 causes compressed air or oxygen to flow at high velocity through the medicine to turn it into an aerosol. The nebulizer 52 is in fluid communication with the facemask 10, 10' via the port 20, and the aerosol may be inhaled by the patient via the opening 18. Some embodiments of the present invention are directed to assemblies and systems that include the facemask 10 or 10' and a nebulizer (e.g., the nebulizer assembly 50).

Figure 5:
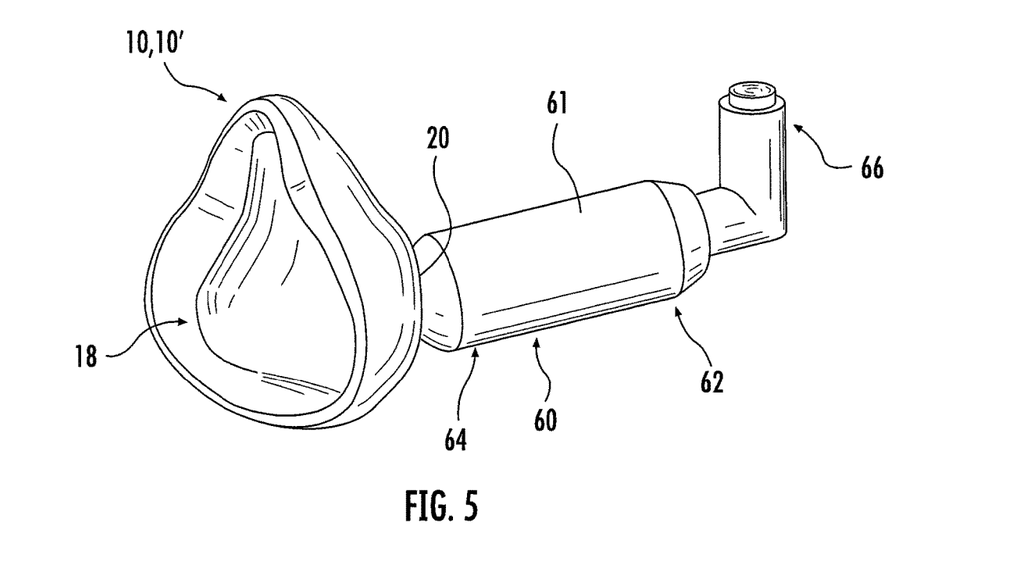
FIG. 5 is a perspective view of a facemask connected to a spacer and a metered dose inhaler (MIDI) according to some embodiments of the invention.

Facemasks 10, 10' according to embodiments of the present invention may be suitable for use with a spacer or a valved holding chamber used in connection with an MDI or a pMDI. A spacer 60 is shown in FIG. 5. The spacer 60 has an elongated body 61 with first and second opposed end portions 62, 64. The first end portion 62 is adapted to receive an MDI or a pMDI 66. The second end portion 64 is adapted to operatively connect with the facemask 10, 10' (e.g., via the port 20). In this regard, MDI 66 is in fluid communication with the facemask 10, 10', and medicament released from the MDI upon actuation of the MDI may be inhaled by a patient via the first opening 18.

Figure 6:
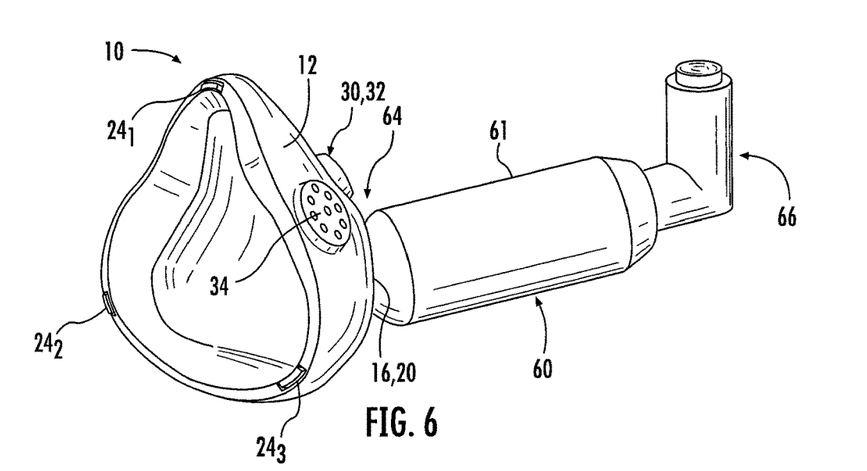
FIG. 6 is a perspective view of an exemplary facemask connected to an MDI spacer according to some embodiments of the invention.
Figure 7A:
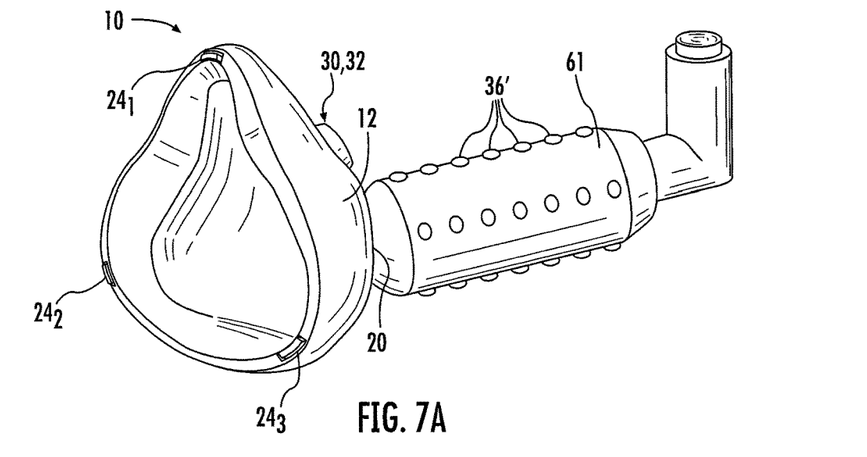
FIG. 7A is a perspective view of a facemask connected to an alternative MDI spacer according to some other embodiments of the invention.
Figure 7B:
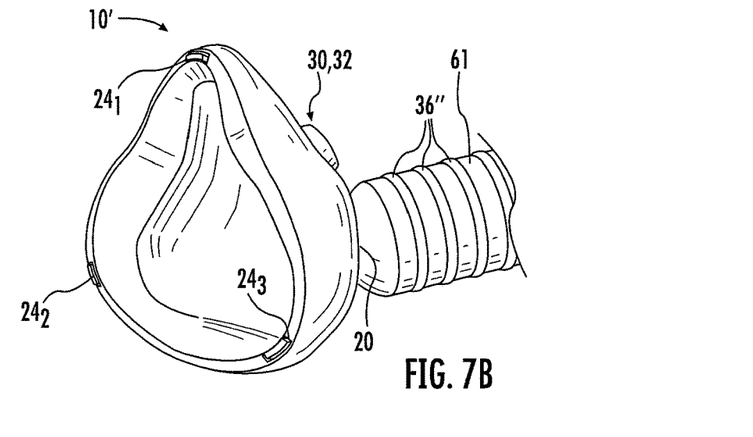
FIG. 7B is a partial perspective view of the facemask of FIG. 7A used with a further alternative MDI spacer according to some embodiments of the invention.

Exemplary facemasks 10, 10' that may be used with MDI spacers are illustrated in FIGS. 6, 7A and 7B. In this embodiment, the port 20 is disposed on the second or forward end 16 of the facemask body 12. The second end portion 64 of the spacer body 61 may be connected to or operatively connected to the port 20. This provides an "in-line" orientation of the facemask 10, 10' and the spacer 60, which may be desirable with the use of spacers or valved holding chambers.

The facemask 10' (FIGS. 7A and 7B) includes the electrical contacts or inputs $24_1$, $24_2$, $24_3$ but the light emitting units can be disposed on the spacer body 61 as opposed to on the facemask body 12. As shown in FIG. 7A, a plurality of discrete LEDs 36' may be arranged around a circumference of the spacer body 61 and/or along at least a portion of a length of the spacer body 61. As shown in FIG. 7B, at least one light string 36" (e.g., LED light string) may be disposed on the spacer body 61 and arranged around a circumference of the spacer body 61. For example, at least one light string 36" may be helically disposed along the spacer body 61 or a plurality of light strings 36" may be annularly disposed around the spacer body 61 in a spaced-apart relationship. It is contemplated that a speaker (e.g., the speaker 34 shown in FIG. 6) may be employed in connection with the facemask 10'. The speaker may be disposed on the facemask body 12, on the spacer body 61 or on some other component, such as an intermediate component between the spacer 60 and the facemask 10', or may otherwise be attached to or in communication with the facemask 10'.

The power supply 30 and controller 32 are shown as disposed on the facemask body 12 in FIGS. 6, 7A and 7B. It is contemplated that one or both of these components may be disposed on the spacer body 61, or on an intermediate component between the facemask 100' and the spacer 60. In this regard, conductive wires, traces or flex circuit(s) may run from each of the electrical contacts or inputs $24_1$, $24_2$, $24_3$ to the power supply 30, for example.

The facemasks 10, 10' used with spacers can provide similar stimuli to the spacers 10, 10' used with nebulizers. An advantage of having similar stimuli on both nebulizer and spacer facemasks is that a child may be transitioned from one device to another, which usually occurs around age six.

Figure 8:
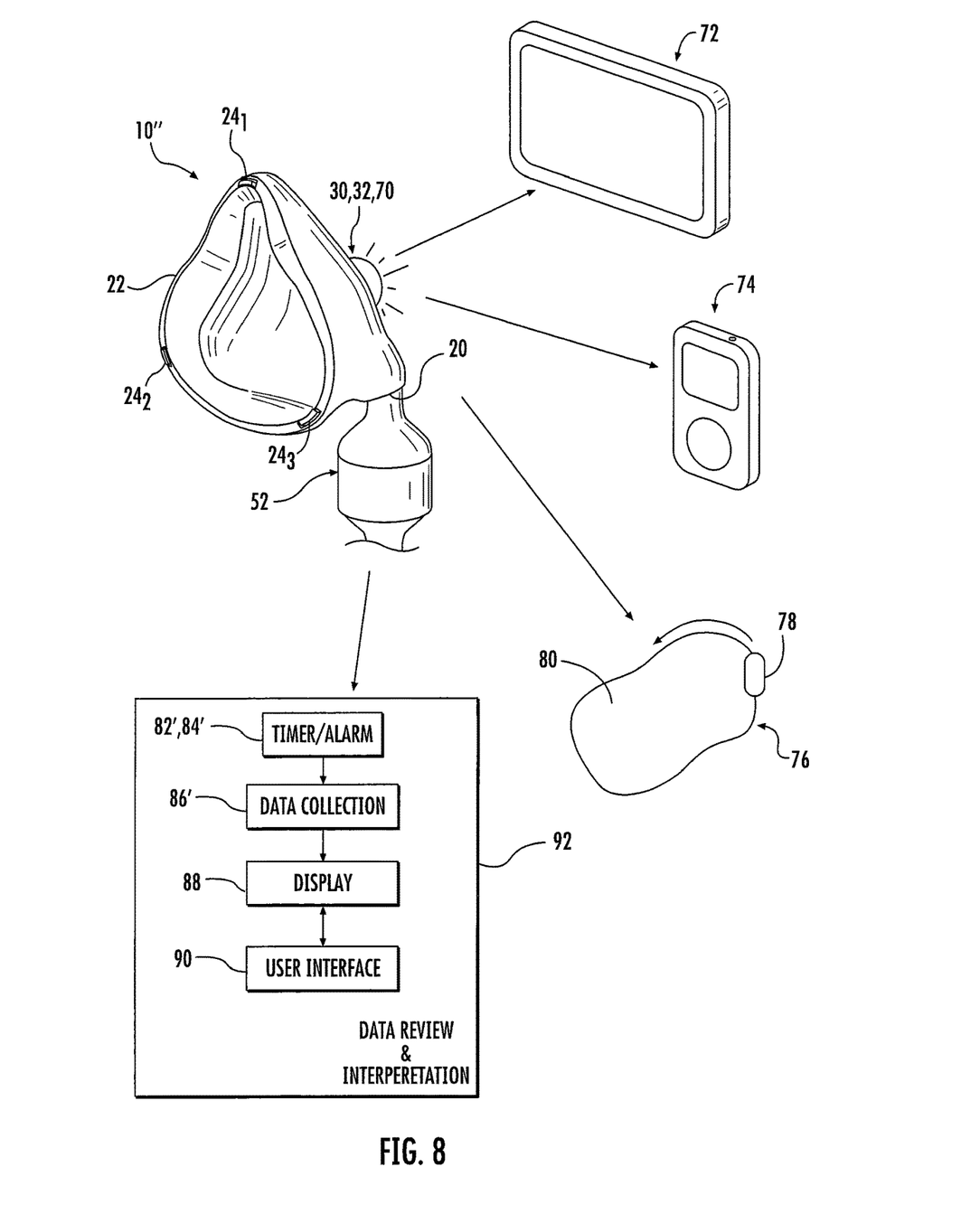
FIG. 8 is a perspective view of an exemplary facemask configured to wirelessly communicate with one or more devices according to some embodiments of the invention.

A facemask 10" according to some other embodiments of the invention is shown in FIG. 8. Like the previously described facemasks, the facemask 10" includes electrical contacts or inputs $24_1$, $24_2$, $24_3$ to sense whether a patient's face is sealingly engaged with the skin contact perimeter 22 of the facemask 10". The facemask 10" includes a wireless transmitter 70. In response to receiving a concurrent signal from each of the plurality of electrical contacts or inputs $24_1$, $24_2$, $24_3$, the power source 30 is electrically connected to the controller 32, which in turn controls the wireless transmitter 70 to establish a wireless connection with and transmit wireless signals to one or more outside devices that can provide audible and/or visual stimulus. The wireless connection may be any suitable wireless connection such as a radio frequency (RF) connection, a Bluetooth® connection, a wireless local area network connection (e.g., 802.11) and the like.

The transmitter 70 may establish a wireless connection with and transmit wireless signals to a display device 72 that is configured to receive wireless signals and, in response, output visual stimulus and, optionally, audible stimulus. For example, the display device 72 may be a monitor, television, smartphone or a tablet computer. The display device 72 may be configured to play children's movies, children's shows and the like.

The transmitter 70 may also establish a wireless connection with and transmit wireless signals to an audio or music storage device 74 that is configured to receive wireless signals and, in response, to output audible stimulus. The device 74 may be an MP3 player, an iPod®, a smartphone and the like. The device 74 may be loaded with melodies, songs, children's stories and so forth. At least one of the devices 72, 74 may be a smartphone, tablet computer or the like configured to run applications that may provide the audible and/or visual stimuli and that may monitor and/or store data associated with facemask compliance.

The transmitter 70 may also establish a wireless connection with and transmit wireless signals to a toy 76 that is configured to receive wireless signals and, in response, to activate thereby providing visual and/or audible stimulus. As just one example, the toy may be a train 78 that is configured to advance along a track 80 in response to receiving wireless signals from the transmitter 70.

Although not illustrated, it is contemplated that the facemasks 10, 10', 10" described above may be configured to receive a wire or cable so as to establish a wired connection to an outside device, such as the devices 72, 74, 76 shown in FIG. 8. As described above, the devices 72, 74, 76 can output audible and/or visual stimuli when the facemask is sealingly engaged with a patient's face.

The devices 72, 74, 76 may serve to hold a child's attention an extended period of time to facilitate proper positioning of the facemask during the entire treatment. This may be useful with nebulizer therapy, for example, which often requires 15-30 minutes to deliver a dose of therapeutic aerosol.

Figure 9A:
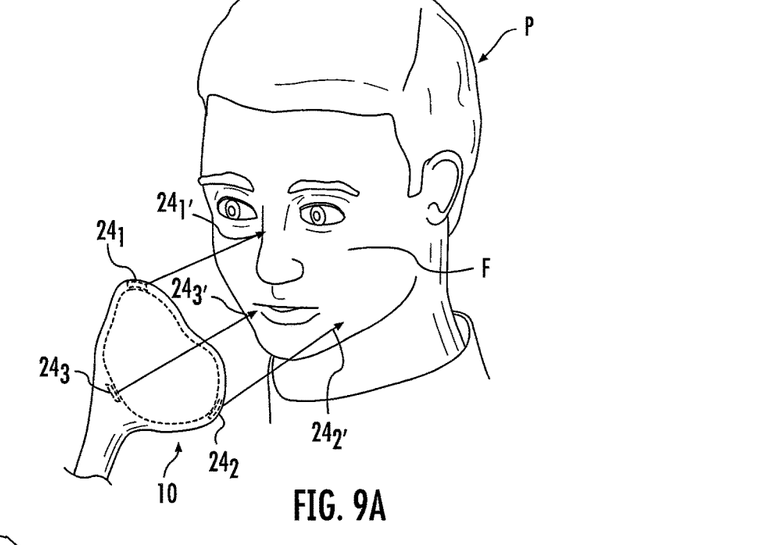
FIG. 9A is a schematic illustration showing exemplary contact points of a facemask for a respective patient's face according to embodiments of the invention.
Figure 9B:
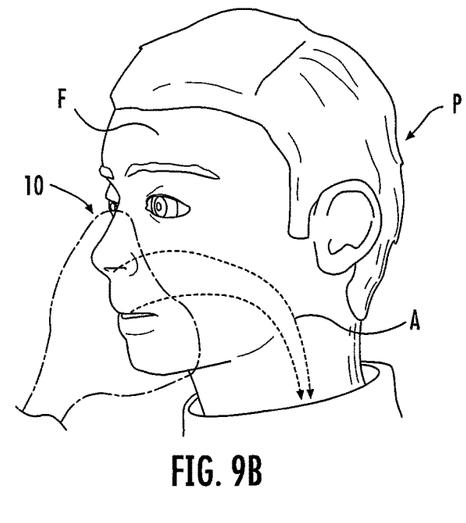
FIG. 9B is a schematic illustration showing the facemask of FIG. 9A sealingly engaged with the patient's face.

As discussed above, at least three spaced-apart switches $24_1$, $24_2$, $24_3$ may be employed on the facemasks 10, 10', 10" to enhance compliance. Multiple points of contact are desirable in order to accurately determine that a proper seal has been established so that aerosol may be effectively delivered to the patient. As shown in FIG. 9A, as the facemask 10 is brought toward a face F of a patient P, each one of the switches $24_1$, $24_2$, $24_3$ contact the patient's face F at a respective point $24_1'$, $24_2'$, $24_3'$. For example, and as illustrated, the contact point $24_1'$ may be on the bridge of the patient's nose and the contact points $24_2'$, $24_3'$ may be on opposite sides of the patient's mouth (e.g., on opposite cheeks). Therefore, in some embodiments, when the facemask is sealingly engaged with a patient's face, one of the switches $24_1$ is actuated by the bridge of the patient's nose and two of the switches $24_2$, $24_3$ are actuated by the patient's face on opposite sides of the patient's mouth. FIG. 9B shows the facemask 10 sealingly engaged with the patient's face F. With the facemask 10 sealingly engaged with the patient's face F, the aerosol medication (shown as A) is effectively inhaled by the patient P with little to no waste.

Figure 9C:
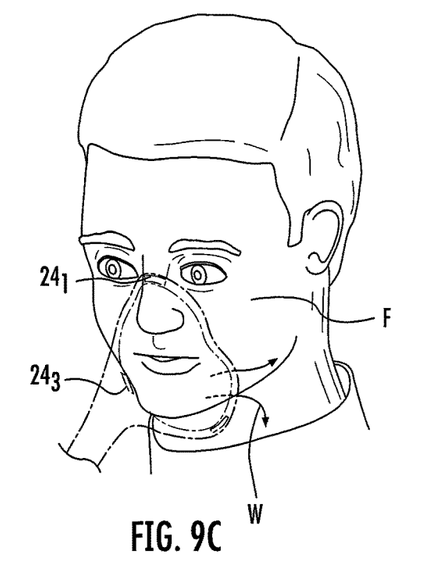
FIG. 9C is a schematic illustration showing the facemask of FIG. 9A that is not sealingly engaged with the patient's face and which can be electrically detected due to insufficient electrical contact according to embodiments of the invention.

On the other hand, and as shown in FIG. 9C, if the facemask is not properly sealed with the patient's face, there will be aerosol waste, shown as W. FIG. 9C illustrates that the positioning and functionality of the switches $24_1$, $24_2$, $24_3$ may advantageously determine when a suitable seal has been established. As shown in FIG. 9C, only the switches $24_1$, $24_3$ are in contact with skin, and therefore a lack of seal near where switch $24_2$ would have been positioned is not detectable. It is contemplated that as few as two switches may be employed, for example the switches $24_2$, $24_3$, as a facemask may be configured to conform around and above the patient's nose. It is also contemplated that more than three switches may be provided, for example 4, 5, 6, 7, 8, 9, 10 or more switches. It is believed that three switches establish a suitable number of contacts to accurately detect whether the facemask is sealingly engaged with the patient's face.

Referring back to FIG. 2, a timer 82 and/or an alarm 84 may be employed. The timer 82 may be electrically connected with the electrical contacts $24_1$, $24_2$, $24_3$ and/or the control circuit 28 (e.g., the power source 30 and/or the controller 32). The timer 82 may be configured to measure or an amount of time or a duration that the facemask 10, 10', 10" is sealingly engaged with the patient's face; that is, the amount of time a concurrent signal is received from each of the plurality of electrical contacts $24_1$, $24_2$, $24_3$. In some embodiments, the timer 82 is integrated with the controller 32. In some embodiments, the controller 32 is configured to measure the amount of time or duration that the facemask is sealingly engaged with the patient's face and the timer 82 may be omitted.

The alarm 84 may receive an alarm signal from the timer 82 and/or the controller 32. The alarm 84 may be configured to receive the alarm signal and provide an audible and/or visual alert when a certain event has occurred. For example, the alarm 84 may output an audible and/or visual alert when the amount of time or duration a concurrent signal received from the electrical contacts $24_1$, $24_2$, $24_3$ (indicating that the facemask 10, 10', 10" is sealingly engaged with the patient's face) reaches or exceeds a predetermined threshold value. The threshold value may be known by or stored in the timer 82 and/or the controller 32 and, in some embodiments, may be user selectable. In this regard, the alarm 84 may provide an alert when the appropriate amount of medication has been delivered to the patient. The alarm 84 may also output an audible and/or visual alert when the amount of time or duration a concurrent signal received from the electrical contacts $24_1$, $24_2$, $24_3$ does not reach the threshold value. In this situation, the alarm 84 may provide an alert that the facemask 10, 10', 10" has become disengaged and that attention should be given to the patient. In some embodiments, the speaker 34 and/or the LEDs 36, 36', 36" may be configured to output the audible and/or visual alerts and a separate alarm component may not be needed.

The controller 32, the timer 82 and/or the alarm 84 may communicate with a data collection system or a memory 86 that is configured to collect data associated with the use of the facemask 10, 10', 10". The data collection system 86 may collect data such that duration and continuity of medication delivery may be monitored (e.g., by medical staff or some other supervisor). The data may indicate the length of time the facemask was sealingly engaged with the patient's face and may indicate any "gaps" during treatment (e.g., removal or disengagement of the facemask) so that compliance may be monitored and/or reviewed. A connection or port 87 may be provided for connection of a device to retrieve data from the data collection system 86. As one example, the connection 87 may be a USB port configured to receive a memory stick or thumb drive, which may then be connected to a personal computer or other device such that the retrieved data may be reviewed and analyzed. As another example, the connection 87 may allow direct connection to a device such as a tablet computer, smartphone or the like. The data may be provided to the device dynamically such that the data may be viewed in real time. It may also be stored on the device for later review.

Where used, the timer 82, the alarm 84, the data collection system 86 and/or the connection 87 may be disposed on the facemask body 12 or elsewhere as described above in connection with the power source 30 and the controller 32. Thus, the continuity and/or duration of medication delivery and data associated therewith may be monitored at or near the facemask 10, 10', 10".

In some embodiments, and as shown in FIG. 8, the facemask 10" may wirelessly communicate with a device 92. The device 92 may include a timer 82', an alarm 84', a data collection system or memory 86', a display 88 and/or a user interface 90. For example, in response to receiving a concurrent signal from each of the plurality of contacts $24_1$, $24_2$, $24_3$, the wireless transmitter 70 may establish a connection and transmit a wireless signal to the device 92, and the timer 82' and/or the alarm 84' may provide the functionality of the timer 82 and/or the alarm 84 as described above. The data collection system 86' may collect data associated with the use of the facemask 10" in the same manner described above in connection with the data collection system 86. The display 88 may be used to display the data from the data collection system 86' in real time; alternatively, a user may review and interpret data on the display 88 at a later time. A user may use the user interface 90 to interpret, manipulate and/or review the data on the display 88. The user interface 90 may be integrated with the display 88 (e.g., a touch display).

The device 92 may be a personal computer, tablet computer, smartphone or the like to generally monitor and store data associated with facemask compliance. It is contemplated that one or more of the timer 82', the alarm 84' and/or the data collection system 86' may be omitted or its equivalent may be provided at or near the facemask 10" as described above. For example, the data collection system 86 may be provided at or near the facemask 10" and data from the data collection system 86 may be wirelessly transmitted by the transmitter 70 to the device 92.

The facemasks described herein can improve juvenile patient compliance with inhaled medication administration. The contact switches help ensure that the audible stimulus and/or visual stimulus are provided only when a proper seal has been established and is maintained. The audible stimulus and/or visual stimulus can help hold a child's attention during dosing. The child may become discouraged when the audible stimulus and/or visual stimulus is halted due to the child removing the mask, and therefore the child may learn to retain the mask in place during treatment. The facemasks may enhance the experience for the child by employing the audible stimulus and/or visual stimulus (e.g., distractions) to encourage continuous placement of the mask, and thereby improve patient compliance and effective delivery of the drug.

The multiple contact switches providing multiple points of contact help establish that a proper seal is established and maintained. Properly sealed contact with the face not only helps with compliance but also helps to prevent exposure of leaked aerosol to the eyes and other portions of the face. Efficacy may be increased over existing facemasks that provide little to no incentive to keep the mask in place. Waste may be reduced because the drug is inhaled more efficiently. The time for treatment may also be reduced; for example, the time for relief of asthmatics may be minimized.

Furthermore, the facemasks according to embodiments of the present invention do not substantially change the morphology of existing facemasks. As such, facemasks according to embodiments of the present invention can be used with virtually any nebulizer and MDI spacer. The facemasks can be used with pediatric patients for virtually any disease that requires aerosol therapy including asthma, cystic fibrosis and pulmonary exacerbations of infectious disease. The facemasks generally improve patient compliance, ease of use (e.g., trainability), efficiency and efficacy.

Facemasks according to embodiments of the invention may also be useful for training adults that have difficulty with coordination, such as adults with disabilities and/or the elderly. The audible and/or visual stimuli can improve compliance, efficiency and efficacy with these patients, as well.

It will be appreciated that the audio output devices and/or the visual indicators described above may also help a caregiver confirm that the facemask is properly sealingly engaged with the child's face. For example, the LEDs 36 (FIG. 3) may illuminate when the electrical contacts $24_1$, $24_2$, $24_3$ are concurrently actuated to indicate that the facemask 10' is properly sealingly engaged with the child's face. According to some embodiments, the LEDs 36 change color when the electrical contacts $24_1$, $24_2$, $24_3$ are actuated. According to some embodiments, an LED 36 adjacent one of the electrical contacts $24_1$, $24_2$, $24_3$ illuminates or changes color when that electrical contact is actuated.

Figure 10A:
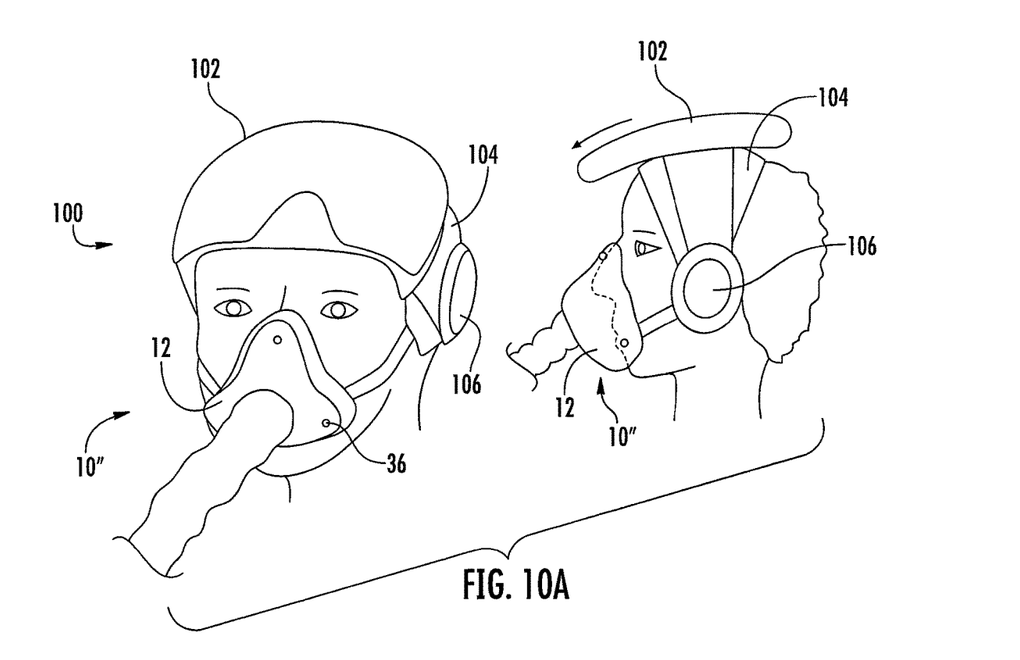
FIG. 10A illustrates a perspective view and a side view of a themed facemask according to some embodiments of the invention.
Figure 10B:
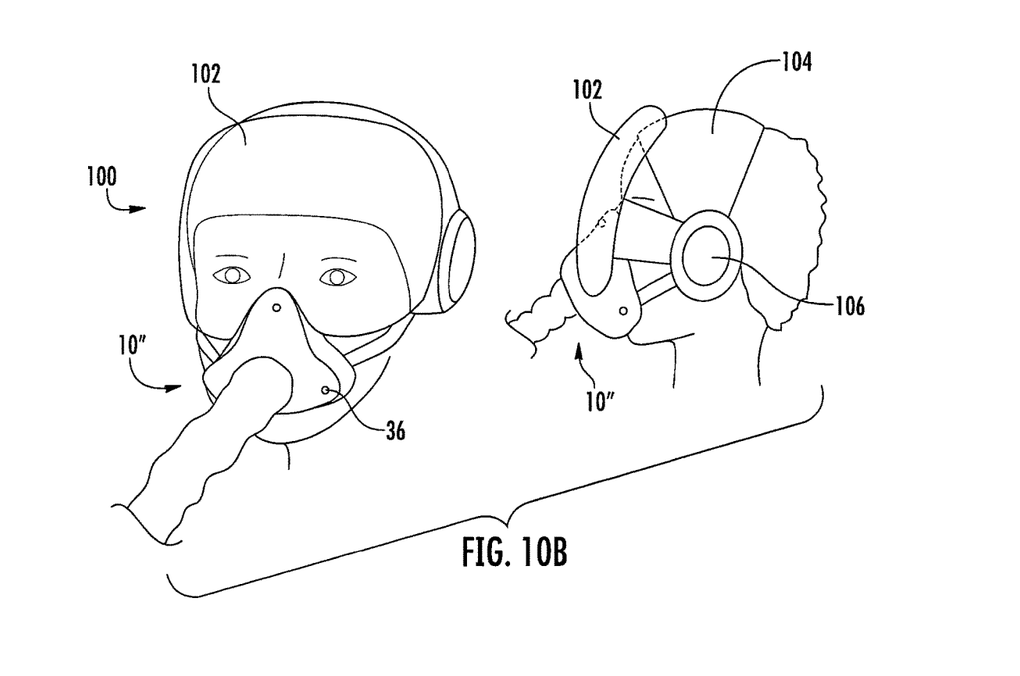
FIG. 10B illustrates a perspective view and a side view of the themed facemask of FIG. 10A with a visor component moved downward.
Figure 11:
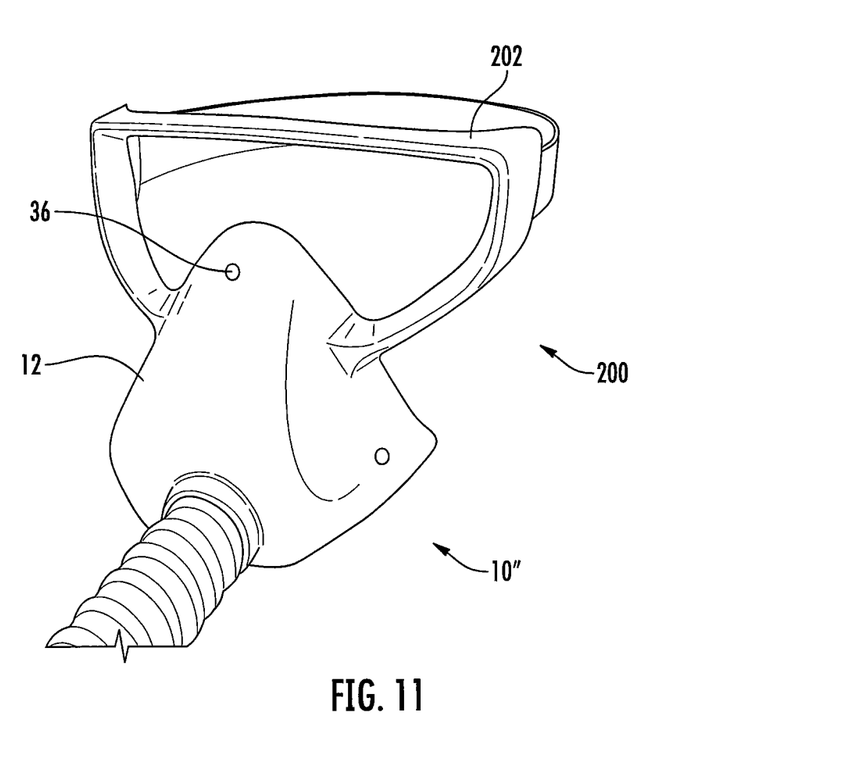
FIG. 11 is a perspective view of a themed facemask according to some embodiments of the invention.

Referring now to FIGS. 10 and 11, the facemask 10" may include the features 100, 200 to have a themed appearance and/or shape.

The feature 100 includes a visor component 102 (which may be a visor or an open frame that may simulate a visor for a child that wears the facemask 10") and a headset component 104 (which may simulate a helmet for a child that wears the facemask 10") to provide a pilot or racecar driver theme. The visor 102 and/or the headset 104 may be integrally formed with the facemask body 12 or may be releasably attachable to the facemask body 12. The visor 102 may be pivotally coupled to the headset 104 such that the visor 102 can be pivoted downwardly from the position shown in FIG. 10A to the position shown in FIG. 10B. The visor 102 may be pivotally coupled to the headset 104 at earphone members 106, which may help hold the facemask in place and optionally may include speakers (e.g., to play audio output for a game played on an outside device as described below).

The feature 200 includes an eye mask or goggles 202 to provide a diver or scuba theme. The eye mask or goggles 202 may be integrally formed with the facemask body 12 or may be releasably attachable to the facemask body 12.

Again, the transmitter or transceiver 70 is configured to wirelessly communicate with the outside device 72 (FIG. 8). As described above, the outside device 72 may be a smartphone, tablet computer or the like and may be configured to display and run a game for a user to play (for example, the game may be included in an application in the memory of the outside device).

As described above, the transmitter 70 of the facemask 10" is configured to transmit a wireless signal (e.g., using a Bluetooth connection) to the outside device 72 when the electrical contacts $24_1$, $24_2$, $24_3$ are concurrently actuated to indicate that the facemask 10" is properly sealingly engaged with the child's face. The outside device 72 may be configured to start a game for the child to play in response to the wireless signal from the transmitter 70 of the facemask 10".

More specifically, the outside device 72 may be configured to start a game for the child to play in response to the wireless signal from the transmitter 70, with the game having a theme that corresponds to the theme of the facemask 10". For example, the facemask 10" and/or outside device 72 may be configured to start and run a flying game involving an airplane to correspond to the pilot theme of the facemask 10" with the feature 100 (FIG. 10). Also, the facemask 10" and/or the outside device 72 may be configured to start and run a diving game involving a (scuba) diver to correspond to the diving or scuba theme of the facemask 10" with the feature 200 (FIG. 11).

The facemask 10" may be configured to stop the game on the outside device 72 when at least one of the electrical contacts $24_1$, $24_2$, $24_3$ is not actuated indicating that at least a portion of the skin contact perimeter 22 is not sealingly engaged with the user's face. According to some embodiments, the wireless transmitter 70 halts the wireless signal to the outside device 72 to stop the game. According to some other embodiments, the wireless transmitter 70 transmits a different wireless signal to the outside device 72 to stop the game.

The facemask 10" may include the controller 30, the timer 82 and/or the alarm 84 as described above to determine whether the amount of time or duration a concurrent signal received from the electrical contacts $24_1$, $24_2$, $24_3$ (indicating that the facemask 10" is sealingly engaged with the patient's face) reaches or exceeds a predetermined threshold value (which value may be user selectable and may be the amount of time for an appropriate amount of medication to be delivered to the patient). The transmitter 70 may halt the wireless signal (or send a different wireless signal) to the outside device 72 to stop the game in response to determining that the predetermined threshold time value has been reached or exceeded. In stopping the game, the outside device 72 may display encouraging images or words to the child, such as displaying fireworks and/or words such as "You Win!"

Therefore, the appearance and design of the facemask 10" may be incorporated in the game played by the child on the outside device 72. The child may be intrigued by the themed facemask 10" and may be encouraged to keep the facemask 10" in place on his or her face due to a feeling of being invested in the game or being part of the game. Once the game is complete, the child or a caregiver can remove the themed facemask 10" and the child may be excited about future uses.

According to some embodiments, the themed appearance of the facemask 10" may be achieved by releasably attaching components to the body 12 of the facemask 10". For example, as described above, the visor 102 and/or the headset 104 may be releasably attachable to the body 12 of the facemask 10" and the eye mask or goggles 202 may be releasably attachable to the body 12 of the facemask 10". In this regard, the facemask body 12 remains the same while also being configured to have differently themed attachments coupled thereto. This may be advantageous in that key features of the facemask (e.g., the shape of the body, the volume of the body, the way that the body sealingly engages the child's face, the way the facemask delivers medicament, etc.) do not change so that regulations (e.g., FDA approval) may not be affected.

It is contemplated that differently themed facemasks and games may be employed. As just one example, the facemask may have an elephant theme (e.g., with a model of an elephant attached to the facemask) and the game may involve an elephant.

It is also contemplated that the facemask 10" may also control a game on the outside device 72 in the same or similar manner as described above but without the themed features 100, 200.

Although facemasks have been described in detail, it is contemplated that various features of the facemasks described above may be advantageously employed with other medicament delivery devices, such as mouthpieces and nasal delivery devices.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A facemask, comprising:
    a facemask body having a first end including an opening configured to receive at least a portion of a user's face and a skin contact perimeter extending along a periphery of the opening, the skin contact perimeter configured to sealingly engage with a user's face;
    a plurality of electrical contacts, each electrical contact disposed at a respective region of the skin contact perimeter, each electrical contact configured to sense when the respective region of the skin contact perimeter is sealingly engaged with a user's face; and
    a control circuit configured to:
        receive a signal from each electrical contact when the respective region of the skin contact perimeter is sealingly engaged with a user's face,
    wherein the control circuit is disposed on the facemask body, and the control circuit is configured to:
        initiate output of an audible stimulus and/or a visual stimulus in response to receiving a concurrent signal from all of the plurality of electrical contacts; and
        stop the audible stimulus and/or visual stimulus when one of the electrical contacts does not sense that the respective region of the skin contact perimeter is sealingly engaged with a user's face.

2. The facemask of claim 1, wherein the facemask body includes a port configured to receive medicament from a medicament delivery device, wherein the opening and the port are in fluid communication such that medicament received in the port can be delivered to the opening.

3. The facemask of claim 2, wherein the port is configured to operatively connect with at least one of a nebulizer and a metered dose inhaler (MDI) spacer.

4. The facemask of claim 1, further comprising a speaker disposed on the facemask body, the control circuit configured to control the speaker to output an audible stimulus.

5. The facemask of claim 4, wherein the control circuit is configured to control the speaker to output a children's melody and/or song as the audible stimulus.

6. The facemask of claim 1, further comprising at least one light emitting diode (LED) disposed on the facemask body, the control circuit configured to illuminate the at least one LED as a visual stimulus.

7. The facemask of claim 1, further comprising a power source disposed on the facemask body, wherein each electrical contact is a switch configured to be actuated when the respective region of the skin contact perimeter is sealingly engaged with a user's face, the switches configured to electrically connect the power source and the control circuit such that, when all the switches are concurrently actuated, the power source is electrically connected with the control circuit to initiate output of the audible stimulus and/or the visual stimulus.

8. The facemask of claim 7, comprising at least three switches spaced-apart along the skin contact perimeter.

9. The facemask of claim 8, wherein the switches are positioned such that, when the facemask is sealingly engaged with a user's face, one of the switches is actuated by the bridge of the user's nose and two of the switches actuated by the user's face on opposite sides of the user's mouth.

10. The facemask of claim 1, wherein each electrical contact is a capacitive sensor configured to detect contact with skin.

11. The facemask of claim 1, wherein the facemask includes a timer configured to measure an amount of time that a concurrent signal is received from all the plurality of electrical contacts and/or to initiate output of an alarm signal when the measured amount of time reaches a threshold value and/or does not reach a threshold value.

12. The facemask of claim 11, wherein the facemask includes a memory configured to store data received from the timer.

13. The facemask of claim 1, further comprising a transmitter disposed on the facemask body, the transmitter configured to transmit a wireless signal to an outside device that is configured to output the audible stimulus and/or the visual stimulus.

14. The facemask of claim 1, further comprising a transmitter disposed on the facemask body, wherein the transmitter is configured to transmit a wireless signal to an outside device when a concurrent signal is received from all the plurality of electrical contacts such that the outside device can display and/or record data based on the wireless signal.

* * * * *